(12) United States Patent
Sato

(10) Patent No.: US 6,932,253 B2
(45) Date of Patent: Aug. 23, 2005

(54) AUTOMATIC GLOVING APPARATUS

(75) Inventor: Hiromi Sato, Yokohama (JP)

(73) Assignee: Misuzu Seiko Kabushiki Kaisha (JP)

( * ) Notice: Subject to any disclaimer, the term of this patent is extended or adjusted under 35 U.S.C. 154(b) by 76 days.

(21) Appl. No.: 10/629,580

(22) Filed: Jul. 30, 2003

(65) Prior Publication Data

US 2004/0149788 A1 Aug. 5, 2004

(30) Foreign Application Priority Data

Jan. 30, 2003 (JP) ........................ 2003-021606

(51) Int. Cl.[7] .............................................. A47G 25/80
(52) U.S. Cl. ........................................................ 223/111
(58) Field of Search .......................................... 223/111

(56) References Cited

U.S. PATENT DOCUMENTS 4,889,266 A * 12/1989 Wight ........................ 223/111
6,053,380 A * 4/2000 Sherrod ...................... 223/111

FOREIGN PATENT DOCUMENTS

JP      2002-224139      8/2002

* cited by examiner

Primary Examiner—John J. Calvert
Assistant Examiner—James G Smith
(74) Attorney, Agent, or Firm—Finnegan, Henderson, Farabow, Garrett & Dunner, L.L.P.

(57) ABSTRACT

An automatic gloving apparatus includes a glove storage portion in which a plurality of gloves are stored. A glove conveying mechanism takes out one of the gloves stored in the glove storage portion and conveys the glove to a hand insertion position where a hand can be inserted into the glove, and a glove holding mechanism opens the mouth of the glove in the hand insertion position so that the hand can be inserted into the glove through the mouth. Air is intermittently blown into the glove held by the glove holding mechanism through an air-blow port provided in the glove holding mechanism.

9 Claims, 17 Drawing Sheets

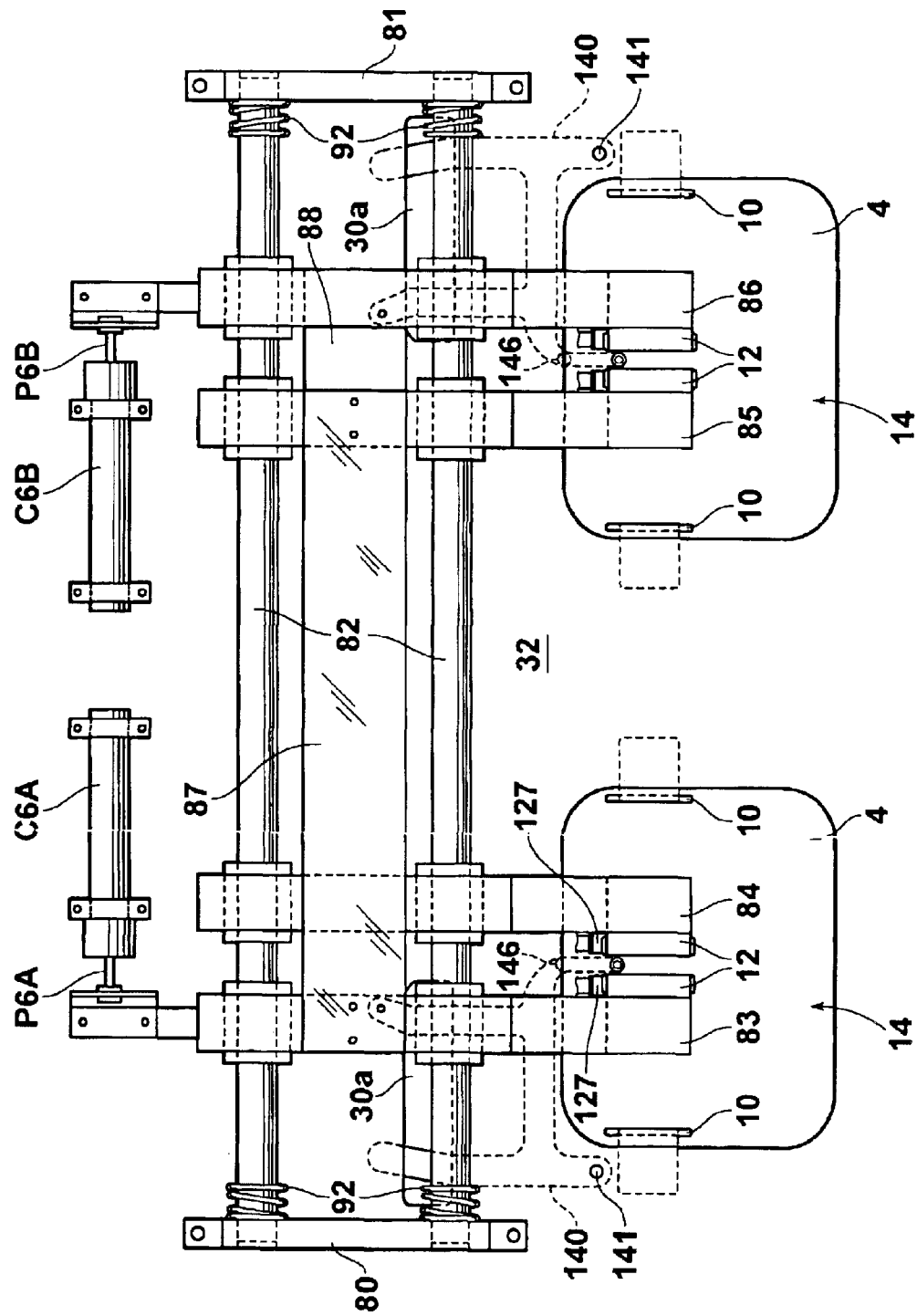

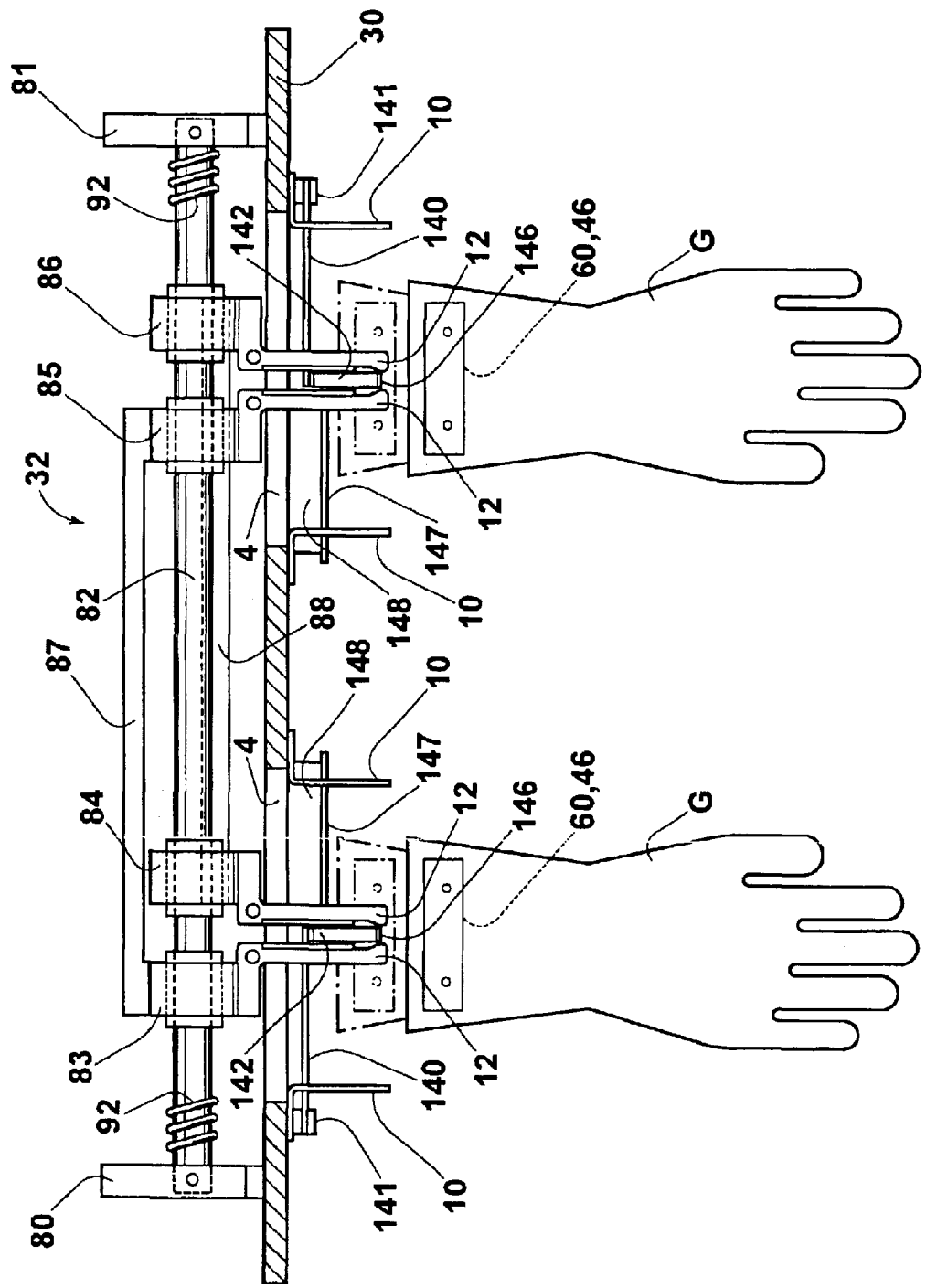

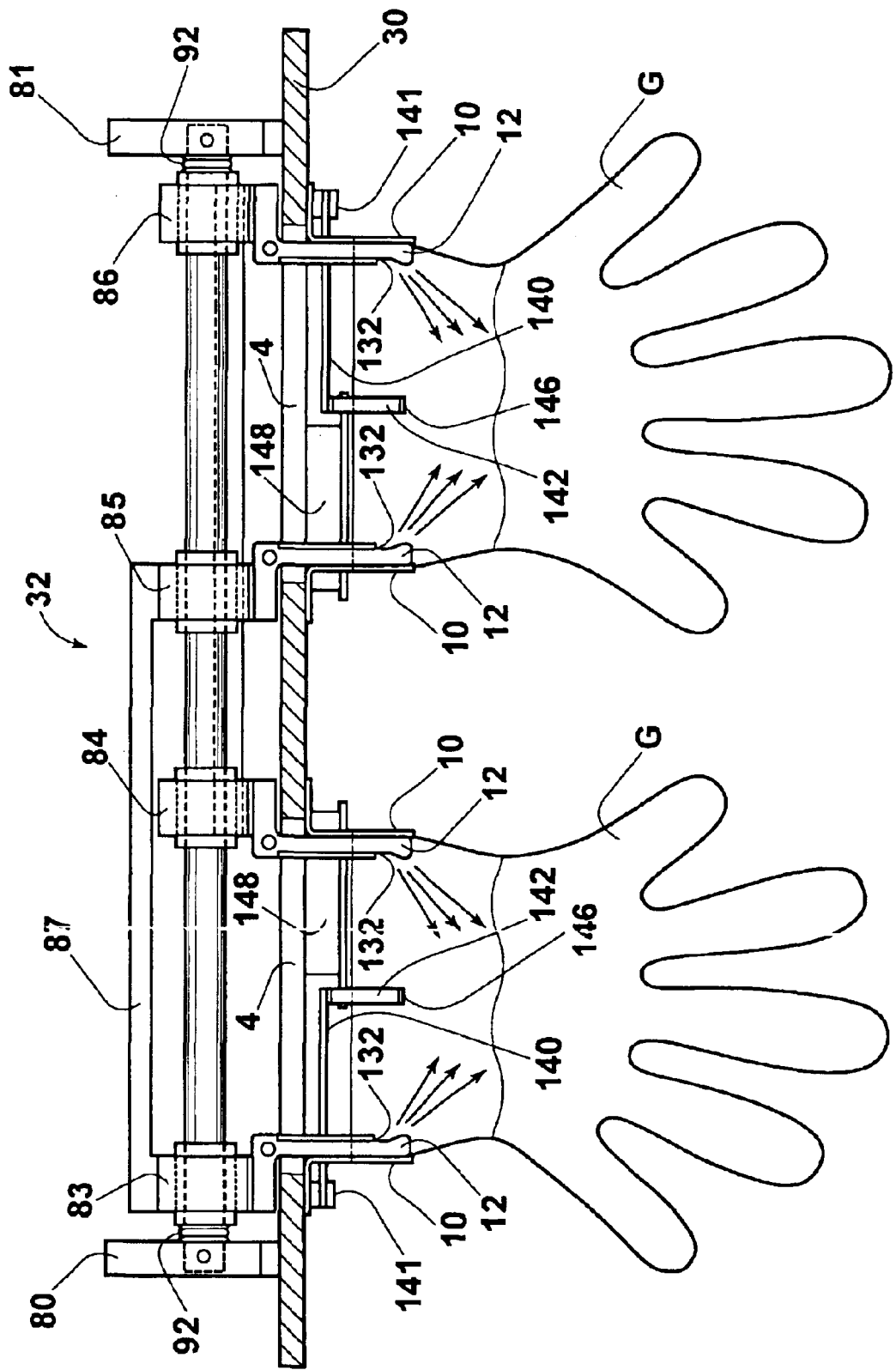

AUTOMATIC GLOVING APPARATUS

BACKGROUND OF THE INVENTION

1. Field of the Invention

This invention relates to an automatic gloving apparatus, and more particularly to an automatic gloving apparatus for automatically putting thin disposable gloves of natural rubber, synthetic rubber, or the like on hands.

2. Description of the Related Art

We, this applicant, has proposed an automatic gloving apparatus as disclosed in Japanese Unexamined Patent Publication No. 2002-224139. The automatic gloving apparatus comprises a glove conveying means which takes out one of gloves stored in a glove storage portion in which a plurality of gloves are stored and conveys the glove to a hand insertion position where a hand can be inserted into the glove, and a glove holding means which opens the mouth of the glove in the hand insertion position so that a hand can be inserted into the glove through the mouth and holds the mouth open, and allows the glove held by the glove holding means to be put on a hand inserted into the glove.

In accordance with the automatic gloving apparatus, hands can be automatically and continuously gloved by simply inserting the hands into predetermined positions, and this can be done continuously. Further the hands can be gloved without touching the surface of the gloves, which is preferred in view of sanitation and disinfection in the case where the gloves are disposable operating gloves used, for instance, in a hospital and food sanitation in the case where the gloves are disposable working gloves used, for instance, in a food processing plant.

Since the automatic gloving apparatus is provided with an air blow means which continuously blows air into the glove for a predetermined time, even a wet hand can be easily inserted into the glove.

However, it has been found that when the hand is in a dripping wet state just after washing the hand or spraying an antiseptic solution, thin gloves of latex, raw rubber, or the like held by the glove holding means can firmly adhere to the hand, and cannot be removed from the hand even if air is blown against the hand, which elongates the time required to glove the hands.

In such a case, in order to smoothly glove the hand, it is necessary to dry the hand with a dryer prior to gloving the hand or to wipe the hand with dry cloth, which deteriorates the working efficiency and gives rise to a sanitary problem.

SUMMARY OF THE INVENTION

In view of the foregoing observations and description, the primary object of the present invention is to provide an automatic gloving apparatus which can readily and rapidly put a glove on a hand even if the hand is in a dripping wet state and the glove is formed of raw rubber and is thin and long.

In accordance with a first aspect of the present invention, there is provided an automatic gloving apparatus comprising a glove conveying means which takes out one of gloves stored in a glove storage portion in which a plurality of gloves are stored and conveys the glove to a hand insertion position where a hand can be inserted into the glove, and a glove holding means which opens the mouth of the glove in the hand insertion position so that a hand can be inserted into the glove through the mouth and holds the glove with the mouth of the glove kept open, wherein the improvement comprises an air blow means which intermittently blows air into the glove held by the glove holding means.

The air blow means intermittently blows air into the glove on a cycle preferably not lower than 3 Hz and not higher than 6 Hz, and more preferably not lower than 4 Hz and not higher than 5 Hz. In this case, the air blow means may comprise an electromagnetic valve which intermittently opens an air passage connecting a pressurized air source and an air blow port on said cycle.

It is preferred that the glove holding means comprises a movable claw which is movable between a stand-by position where it can be inserted into a glove conveyed to the hand insertion position and a glove holding position where it can hold the glove with the mouth of the glove kept open, and said air blow port be provided on the movable claw.

In accordance with a second aspect of the present invention, there is provided an automatic gloving apparatus comprising a glove conveying means which takes out one of gloves stored in a glove storage portion in which a plurality of gloves are stored and conveys the glove to a hand insertion position where a hand can be inserted into the glove, a glove holding means which opens the mouth of the glove in the hand insertion position so that a hand can be inserted into the glove through the mouth and holds the glove with the mouth of the glove kept open, and an air blow means which blows air into the glove held by the glove holding means wherein the improvement comprises that the glove holding means comprises a movable claw which is movable between a stand-by position where it can be inserted into a glove conveyed to the hand insertion position and a glove holding position where it can hold the glove with the mouth of the glove kept open, and the air blow means has an air blow port provided on the movable claw.

In either of the automatic gloving apparatuses of the first and second aspects of the present invention, it is preferred that the glove holding means be provided with a fixed claw which is associated with the movable claw to pinch therebetween the mouth of the glove when the movable claw is moved to the glove holding position.

In either of the automatic gloving apparatuses of the first and second aspects of the present invention, it is preferred that the glove holding means be provided with an expansion means which expands the mouth of the glove, in response to movement of the movable claw from the stand-by position to the glove holding position, in a direction perpendicular to the direction in which the glove holding means opens the mouth.

Since having an air blow means which intermittently (e.g., at 4 to 5 Hz) blows air into the glove held open by the glove holding means, the automatic gloving apparatus in accordance with the first aspect of the present invention is advantageous in that thin gloves of latex, raw rubber, or the like adhering to the hand in a dripping wet state can be separated from the hand by impact of air imparted to the glove by the air blow means, whereby a glove can be readily and rapidly put on a hand even if the hand is in a dripping wet state.

In the automatic gloving apparatus disclosed in Japanese Unexamined Patent Publication No. 2002-224139, air is blown into the glove from above the mouth of the glove through an air blow nozzle provided above the mouth of the glove held by the glove holding means, whereas in the automatic gloving apparatus in accordance with the second aspect of the present invention, the air blow means has an air blow port provided on the movable claw of the glove holding means which can hold the glove with the mouth of the glove kept open, and accordingly, air is blown into the glove from inside the glove below the upper edge of the mouth of the glove, whereby air can inflate the overall glove and reach the tips of the fingers of the glove so that the glove can be easily separated from the hand in a dripping wet state.

By intermittently blowing air through an air blow port provided on the movable claw of the glove holding means, a glove can be more readily and rapidly put on a hand even if the hand is in a dripping wet state by virtue of both the effects of the first and second aspects of the present invention.

By providing an expansion means which expands the mouth of the glove, in response to movement of the movable claw from the stand-by position to the glove holding position, in a direction perpendicular to the direction in which the glove holding means opens the mouth, the mouth of the glove can be opened wider and accordingly, air can be easily flow between the hand and the glove, whereby a glove can be more readily put on a hand even if the hand is in a dripping wet state.

BRIEF DESCRIPTION OF THE DRAWINGS

FIG. 10 is a plan view showing the chuck drive mechanism in a state where the movable claws of the chuck are in the stand-by position, FIG. 11 is a front view showing the chuck drive mechanism shown in FIG. 10, FIG. 13 is a front view showing the chuck drive mechanism shown in FIG. 12, FIGS. 14A to 14D are a front view, a side view, and a plan view of the movable claw and a cross-sectional view taken along line 14D—14D in FIG. 14A.

DESCRIPTION OF THE PREFERRED EMBODIMENTS

Figure 1:
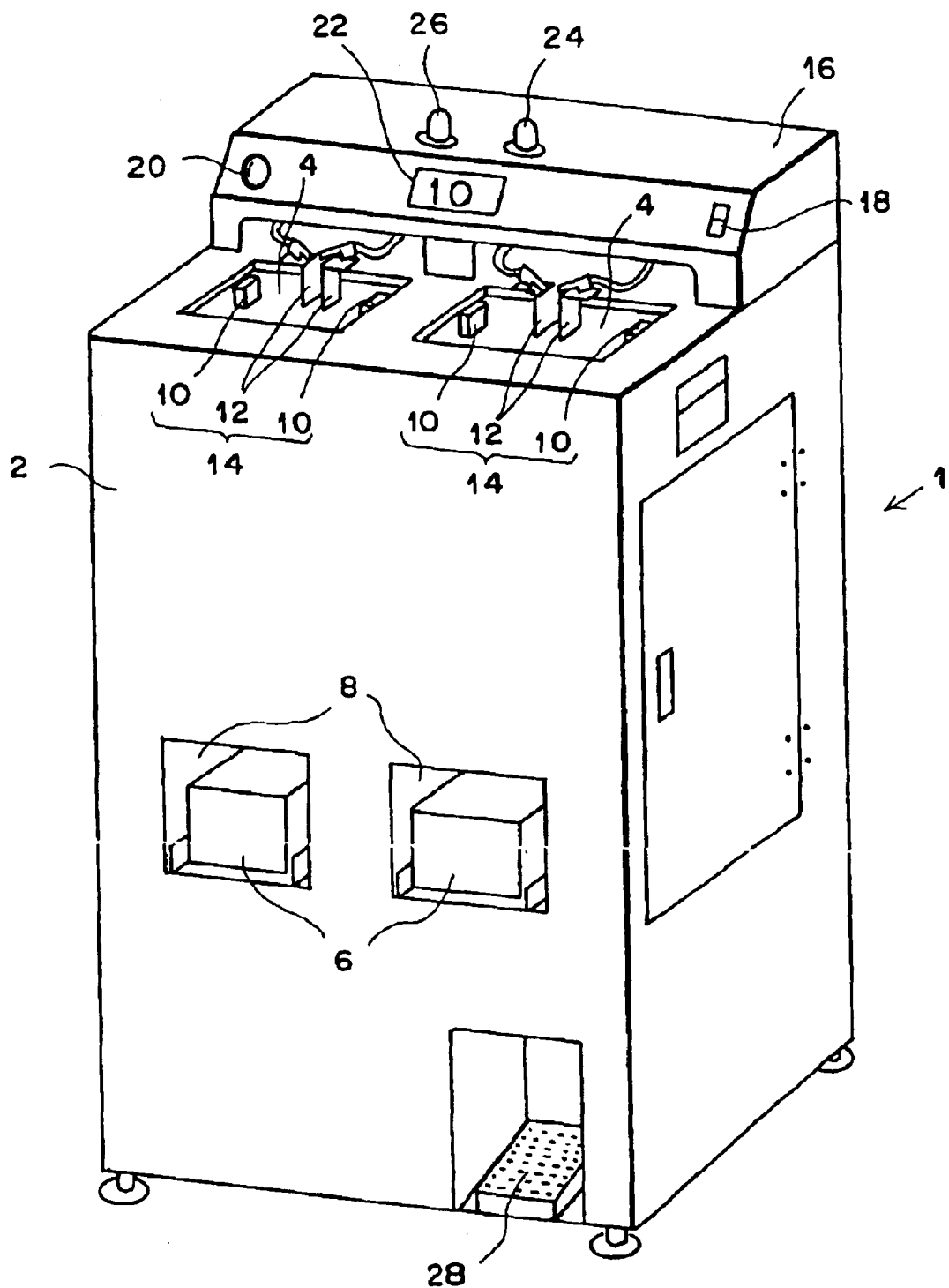
FIG. 1 is a perspective view showing the appearance of an automatic gloving apparatus in accordance with an embodiment of the present invention.

In FIG. 1, an automatic gloving apparatus 1 in accordance with an embodiment of the present invention comprises a housing 2. A pair of hand insertion openings 4 into which left and right hands are inserted open in the top wall of the housing 2, and left and right glove storage portions 8 each of which stores a casing 6 in which a stack 5 of a plurality of elastic and airtight gloves are contained (FIGS. 2 to 4 and 6) open in the front wall of the housing 2.

A chuck 14 is provided inside each hand insertion opening 4. The chuck 14 comprises a pair of stationary claws 10 spaced from each other right and left and a pair of movable claws 12 which are movable right and left between the stationary claws 10. In FIG. 1, the movable claws 12 are in a stand-by position where the movable claws 12 are close to each other at the center of the opening 4. A power switch 18, a power lamp 20, a display window 22 which digitally displays the count of a timer, a NG lamp (red lamp) 24 and an OK lamp (green lamp) 26 are mounted on a panel 16 on the rear side of the openings 4. A foot switch 28 for actuating the gloving apparatus 1 is provided in a lower portion of the housing 2.

Figure 2:
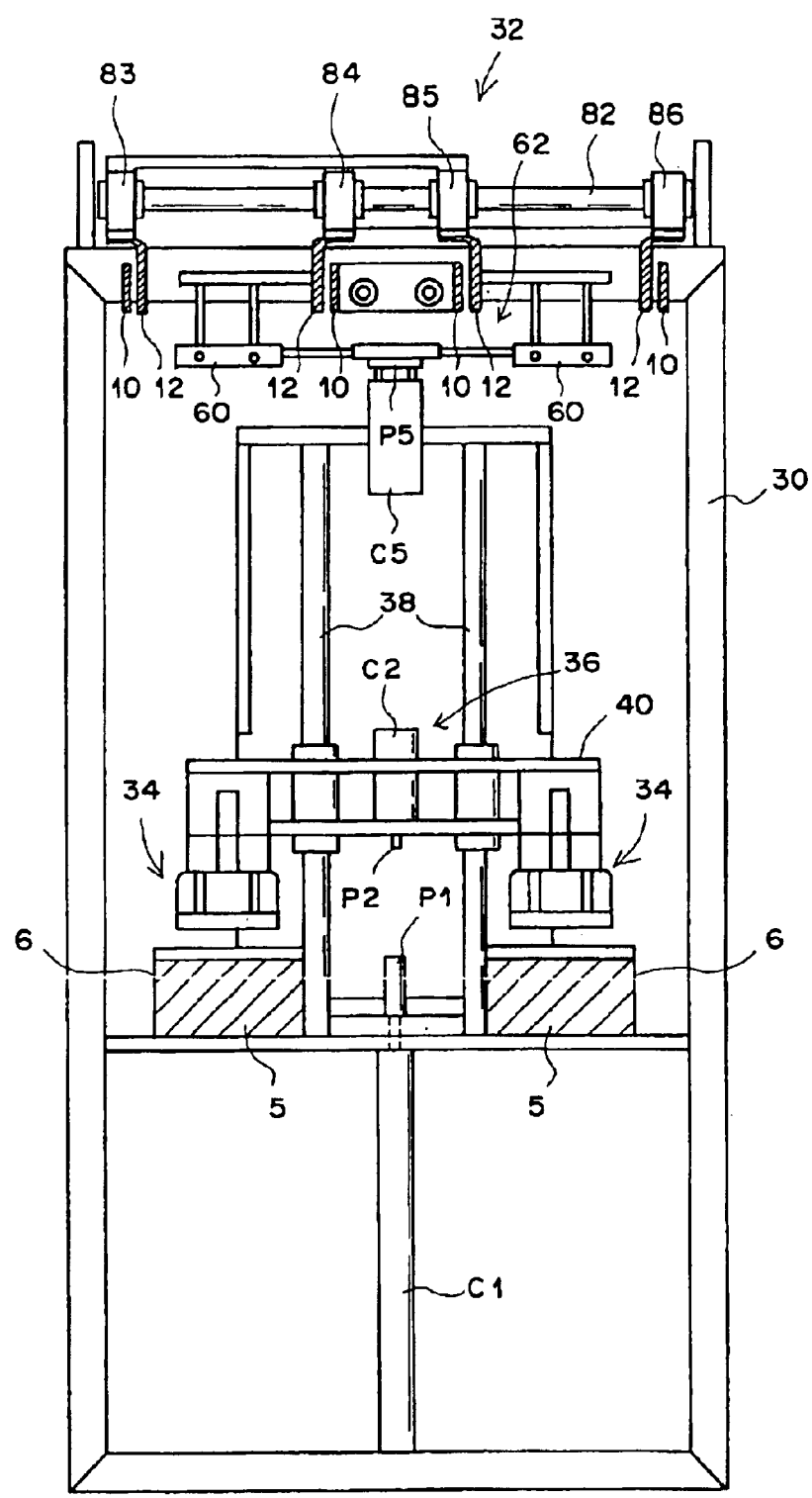
FIG. 2 is a front view showing the inner structure of the automatic gloving apparatus shown in FIG. 1.
Figure 3:
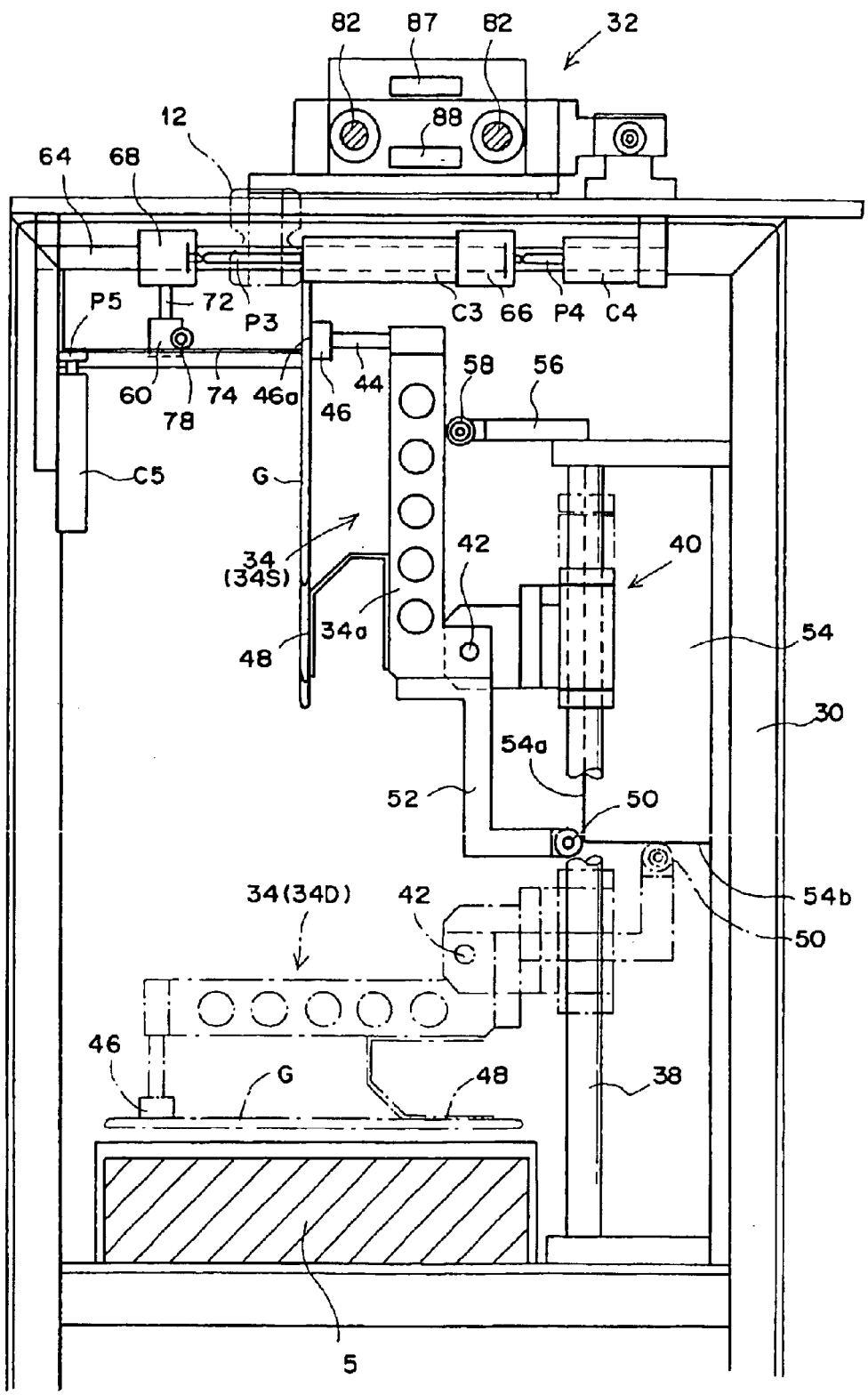
FIG. 3 is an enlarged fragmentary side view showing the inner structure of the upper part of the automatic gloving apparatus shown in FIG. 1.

A chuck drive mechanism 32 to be described later is mounted on the inner side of the panel 16 as shown in FIGS. 2 and 3. The chuck drive mechanism 32 moves the four movable claws 12 in each opening 4 toward each other to the stand-by position shown in FIG. 1 and away from each other to a glove holding position shown in FIG. 2.

A glove conveyor arm 34 which takes out the uppermost glove G one by one from the glove stack 5 in each casing 6 and conveys it upward to a hand insertion position, and an arm drive mechanism 36 comprising long and short air cylinders C1 and C2 for driving the glove conveyor arms 34 are provided in the housing 2.

Figure 4:
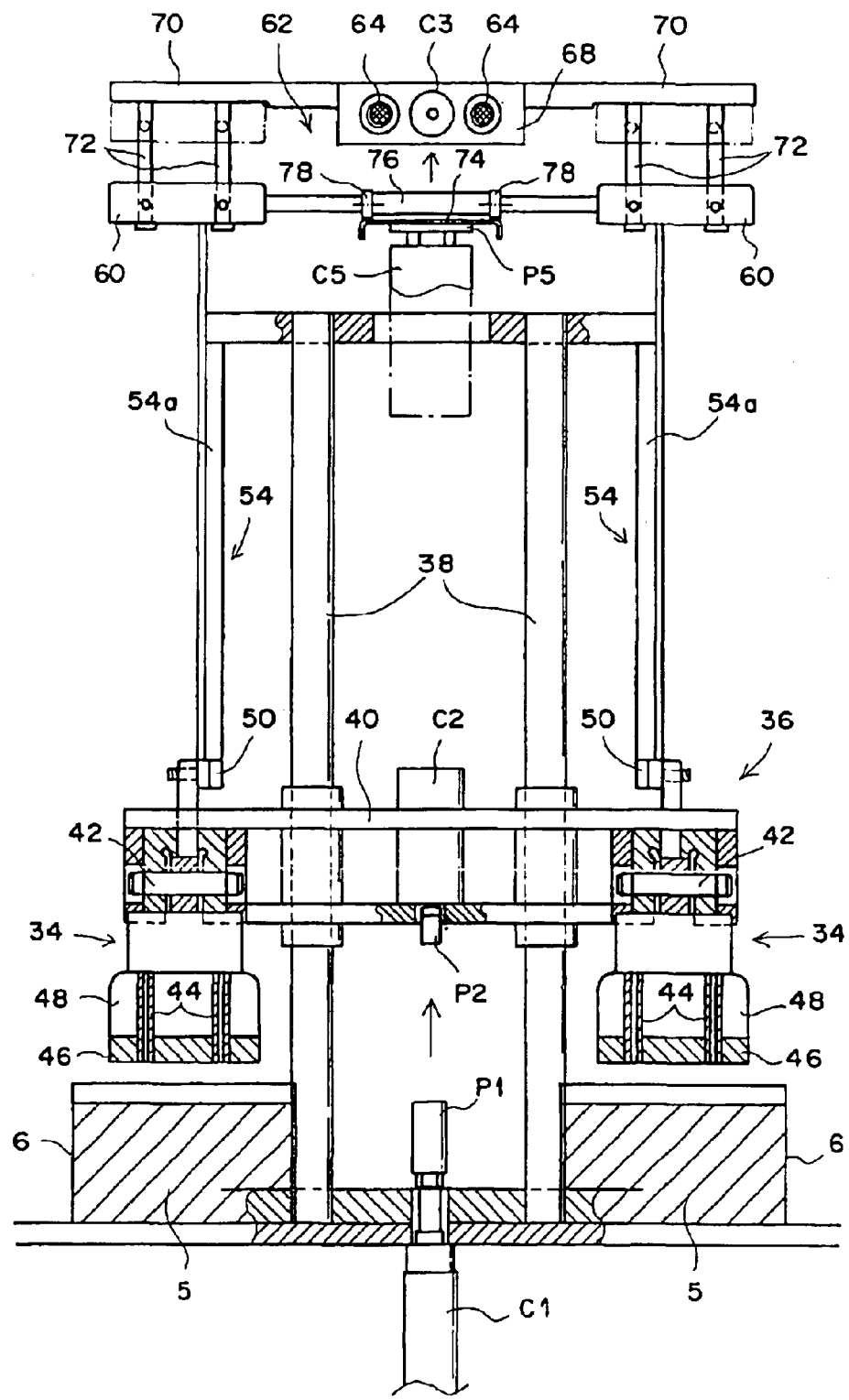
FIG. 4 is an enlarged front view partly in cross-section showing the inner structure of the automatic gloving apparatus shown in FIG. 1.

As clearly shown in FIGS. 3 and 4, the arm drive mechanism 36 further comprises an arm carrier 40 movable up and down along a pair of guide rods 38 vertically erected in the housing 2. The short cylinder C2 is fixed to the center of the arm carrier 40 with its piston rod P2 directed downward. The long cylinder C1 is fixed to the casing 2 below the short cylinder C2 coaxially therewith with its piston rod P1 directed upward.

On the right and left ends of the arm carrier 40 are mounted a pair of shafts 42 extending horizontally right and left. The base end portion of an arm body 34a of each glove conveyor arm 34 is mounted for rotation on each shaft 42.

The glove conveyor arm 34 is provided with a first suction pad 46 which is connected to the free end of the arm body 34a by way of a pair of air pipes 44. An attitude control plate 48 is provided on the base-end side of the arm body 34a. The attitude control plate 48 is brought into contact with the upper surface of the glove stack 5 when the first suction pad 46 is placed on the upper surface of the glove stack 5, thereby keeping horizontal the suction face 46a of the first suction pad 46 and the arm body 34a.

Figure 6:
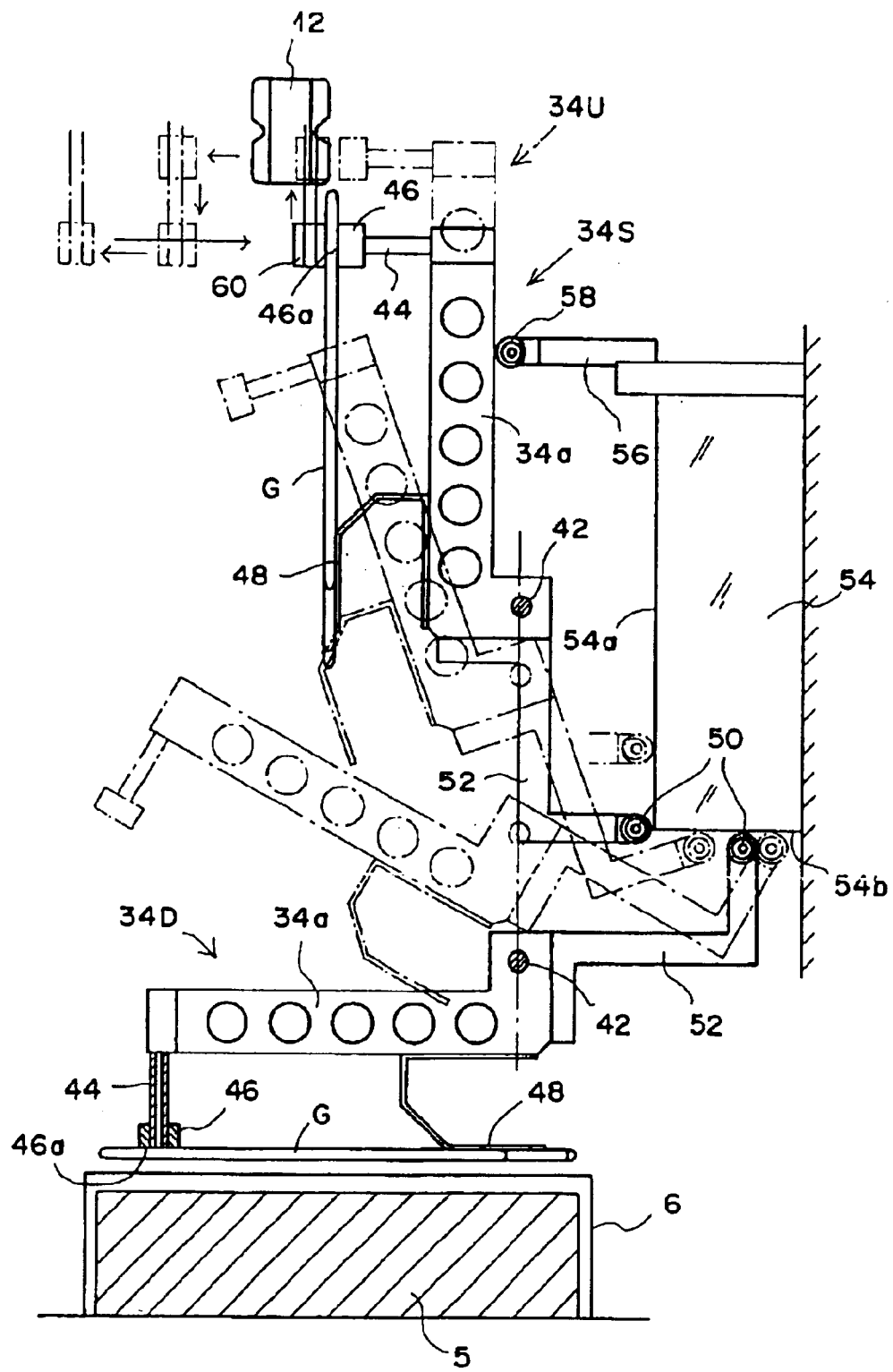
FIG. 6 is a side view showing the action of the glove conveyor arm.

As shown in FIGS. 3 and 6, a sub-arm 52 provided with a cam follower roller 50 at its free end extends from the base end of the arm body 34a, and a cam plate 54 having a right corner where a vertical cam face 54a and a horizontal cam face 54b merge with each other is fixed to the inner surface of the housing 2 opposed to the cam roller 50. A bracket 56 extends horizontally from the upper end of the cam plate 54, and an arm support roller 58 is mounted on the end of the bracket 56.

The glove conveyor arm 34 is moved back and forth between the uppermost position 34U (corresponding to said hand insertion position) shown by the chained line in FIG. 6 and a glove pickup position (not shown) below the lower position 34D shown by the solid line in FIG. 6. Said stand-by position is slightly below the uppermost position 34U as shown by the solid line in FIG. 6 and denoted by 34S. That is, until the gloving apparatus 1 is actuated, the glove conveyor arm 34 is held in the stand-by position 34S with the piston rod P1 of the cylinder C1 projecting upward and the arm body 34a held vertical.

In the stand-by position 34S, the cam follower roller 50 is positioned at the corner of the cam plate 54 between the cam faces 54a and 54b with the arm support roller 58 in contact with the linear back face of the arm body 34a, whereby the arm body 34a is held horizontal with the suction face 46a of the first suction pad 46 and the surface of the attitude control plate 48 held in a vertical plane.

As can be understood from FIGS. 3 and 6, in the stand-by position 34S, since the glove conveyor arm 34 is supported for rotation by the shaft 42 in a position away rightward from the lower end of the arm body 34a and the first suction pad 46 projects leftward from the upper end of the arm body 34a, a counterclockwise rotation moment acts on the glove conveyor arm 34 about the shaft 42.

When the glove conveyor arm 34 is in the stand-by position 34S, the piston rod P1 of the cylinder C1 is held projected upward (retracted downward in the state shown in FIG. 2) and the upper end of the piston rod P1 is in abutment against the lower end of the retracted piston rod P2 of the cylinder C2 to support the arm carrier 40.

When the piston rod P1 of the cylinder C1 is retracted downward in this initial state, the arm carrier 40 moves downward along the guide rods 38 under its own gravity and when the cam follower roller 50 is released from the vertical cam face 54a, the glove conveyor arm 34 is rotated by about 90° in the counterclockwise direction under a counterclockwise rotation moment acting on the arm 34 with the cam follower roller 50 slid on the horizontal cam face 54b, whereby the glove conveyor arm 34 is brought to a lower position 34D where the arm body 34a is held horizontal (FIG. 4).

The arm carrier 40 is further moved downward until the first suction pad 46 on each glove conveyor arm 34 as well as the attitude control plate 48 is brought into contact with the upper surface of the glove stack 5 and then a vacuum is supplied to the first suction pad 46. After the first suction pad 46 holds the uppermost glove G near the mouth thereof under the vacuum, the piston rod P1 is projected upward to return the glove conveyor arms 34 to the stand-by position 34S as shown in FIG. 3.

In the upper portion of the housing 2, there is provided a suction pad drive mechanism 62 comprising a pair of second suction pads 60 which is opposed to the respective first suction pads 46 when the glove conveyor arm 34 is in the stand-by position and cylinders C3 to C5 for moving the second suction pads 60 back and forth and up and down.

Figure 5:
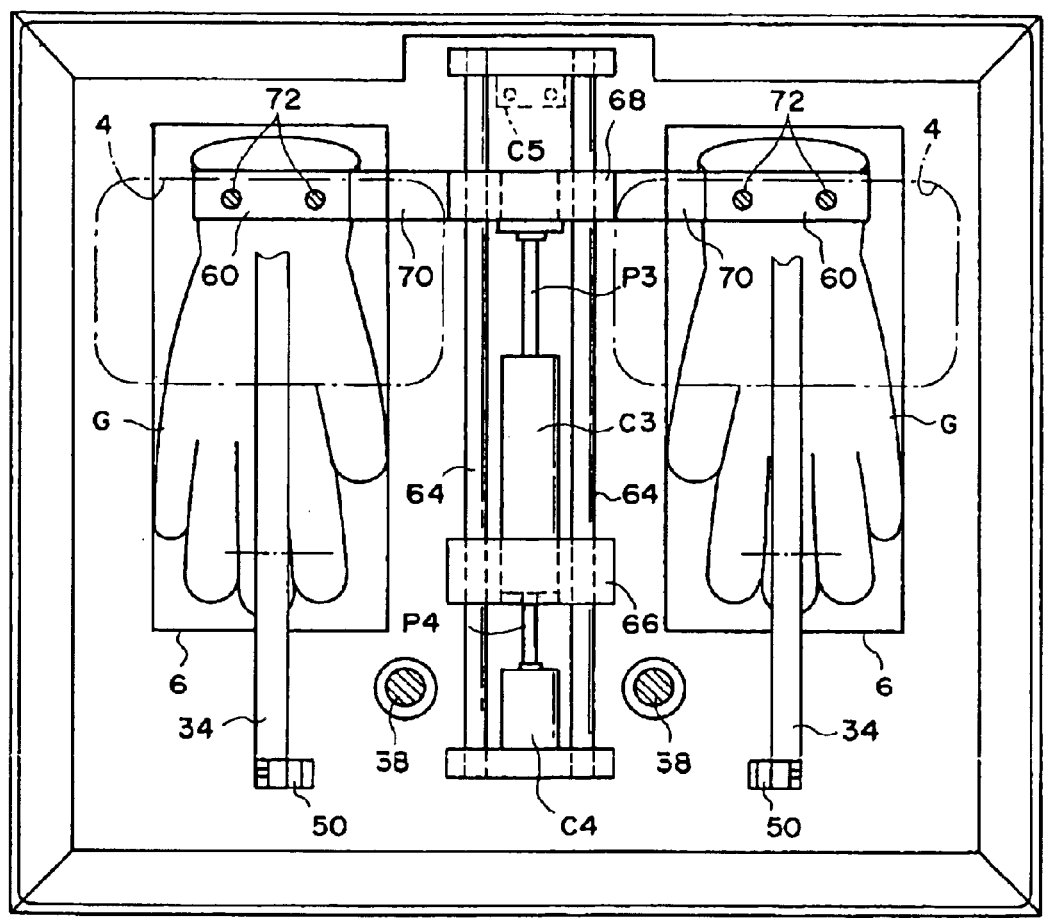
FIG. 5 is a plan view of FIG. 4.

As shown in FIGS. 3 to 5, the suction pad drive mechanism 62 comprises a pair of guide rods 64 extending back and forth transversely spaced from each other, a cylinder carrier 66 which is movable along the guide rods 64 carrying thereon a cylinder C3 fixed thereto between the guide rods 64, a movable table 68 which is movable along the guide rods 64 and is connected to the free end of the piston rod P3 of the cylinder C3, and a cylinder C4 fixed to the housing 2 at one end of the guide rods 64 with its piston rod P4 projected toward the cylinder C3. The free end of the piston rod P4 is connected to the cylinder carrier 66.

A pair of arms 70 extend left and right from the movable table 68. A pair of thin guide rods 72 are suspended downward from each of the arms 70 spaced from each other in the longitudinal direction of the arm 70. The second suction pad 60 is movable up and down along each pair of thin guide rods 72.

A cylinder C5 for moving up and down the second suction pads 60 is fixed to the front wall of the housing 2. A support plate 74 is mounted on the top of the piston rod P5 of the cylinder C5. A pair of rollers 78 mounted on a connecting member 76 which connects the left and right second suction pads 60 are rolled along the support plate 74 in response to movement of the movable table 68 so that the second suction pads 60 are moved up and down by the piston rod P5 by way of the support plate 74.

In its stand-by position, the second suction pads 60 are opposed to the respective first suction pads 46 in the stand-by position. When the second suction pads 60 are in the stand-by position, the piston rod P3 is projected and the piston rods P4 and P5 are retracted.

When the glove conveyor arms 34 are lifted to the stand-by position 34S shown in FIG. 6 by the piston P1 with each of the first suction pads 46 holding by suction the right (as seen in FIGS. 3 and 6) ply of the glove G, the piston rod P3 is retracted to move rearward the movable table 68 along the guide rods 64, whereby the second suction pads 60 are brought into abutment against the left ply of the glove G. Then vacuum is supplied to the second suction pads 60 and the second suction pads 60 hold the left play of the glove G by suction. In this state, the piston rod P4 is projected to move the second suction pads 60 away from the first suction pads 46, whereby the mouths of the gloves G are opened.

Then the piston rod P2 is projected downward and the piston rod P5 is projected upward, whereby the glove conveyor arms 34 are lifted to the uppermost position 34U and the support plate 74 is moved upward. Accordingly, the first and second suction pads 46 and 60 are moved upward and the gloves G are brought to the hand insertion position (the uppermost position) with their mouths opened.

Figure 7A:
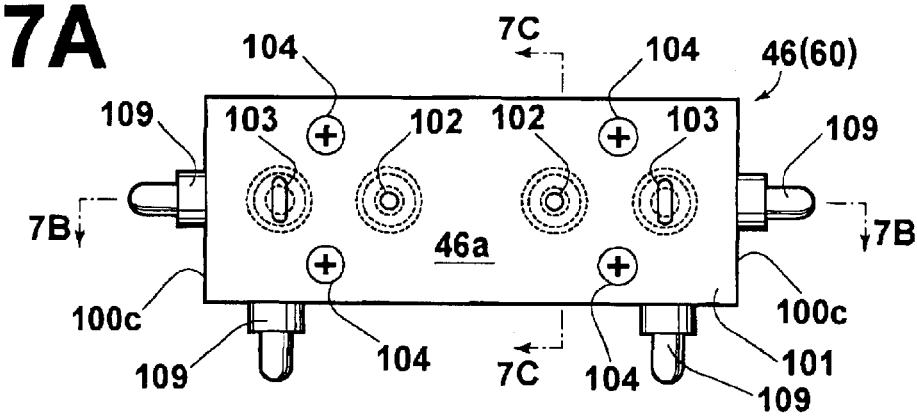
FIG. 7A is a front view showing a preferred structure of the first suction pad.
Figure 7B:
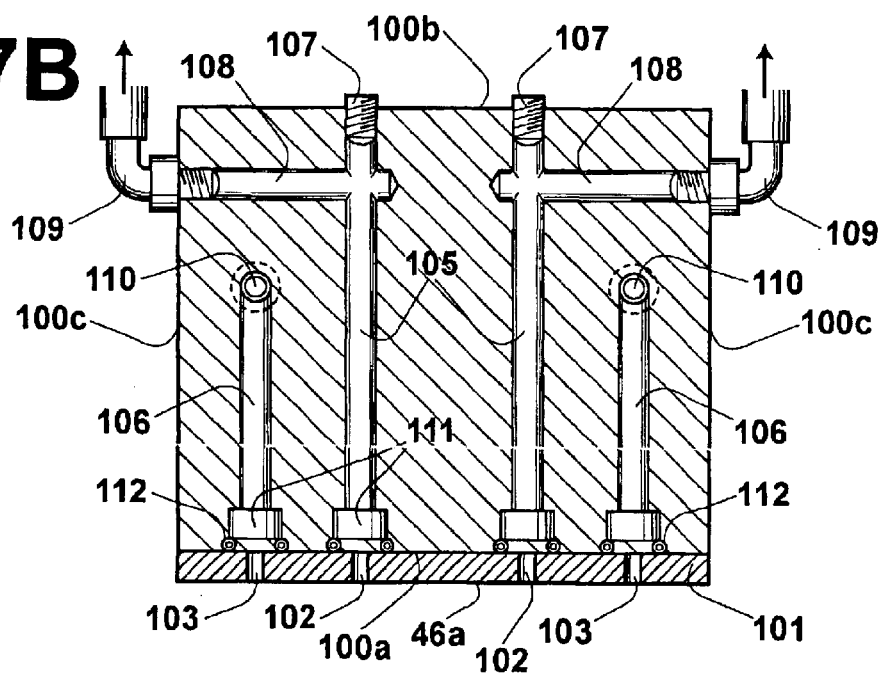
FIG. 7B is a cross-sectional view taken along line 7B—7B in FIG. 7A.
Figure 7C:
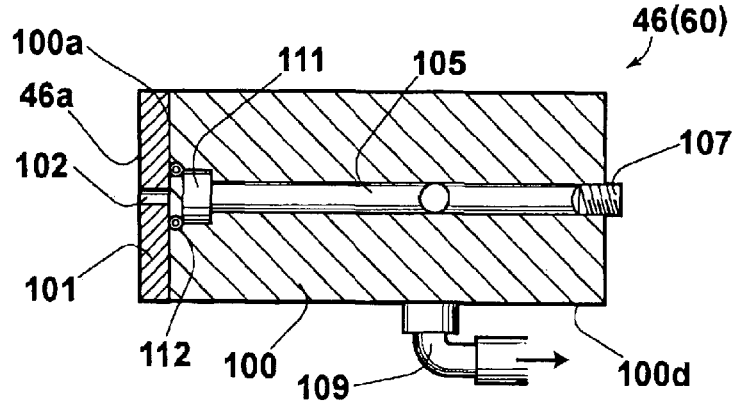
FIG. 7C is a cross-sectional view taken along line 7C—7C in FIG. 7A.

FIGS. 7A to 7C show an example of a preferred structure of the first suction pad 46 (The structure of the second suction pad 60 is the same).

The first suction pad 46 comprises a pad body 100 and a lid member 101 fixed to a flat front face 100a of the pad body 100 by four screws 104, and the front face of the lid member 101 forms the suction face 46a of the first suction pad 46. Four small suction holes are formed in the lid member 101 arranged in a transverse row. The inside two suction holes 102 are circular in cross-section, and the outside two suction holes 103 are vertically elongated in cross-section.

The inside two suction holes 102 are connected to a vacuum source (not shown) by way of air passages 105 and 108. The air passage 105 for each of the inside suction holes 102 reaches the rear surface 100b of the pad body 100 from the front face 100a of the same. The rear end of the air passage 105 is closed by a plug 107 screwed into the rear end portion of the air passage 105. An air passage 108 transversely extends from one of the opposed side faces 100C of the pad body 100 to be connected to the air passage 105 and opens in the side face of the pad body 100. A nipple 109 communicated with the vacuum source is screwed in the open end of the air passages 108.

The outside two suction holes 103 are connected to the vacuum source by way of air passages 106 which extend rearward from the front face 100a of the pad body 100 short of the rear surface 100b. An air passage 110 extends upward from the bottom surface 100D to be connected to each of the air passage 106. A nipple 109 communicated with the vacuum source is screwed in the open end of the air passages 110.

The air passages 105 and 106 communicate with the suction holes 102 and 103 by way of large-diameter portion 111 which are larger in diameter than the suction holes 102 and 103 and the air passages 105 and 106. An O-ring 112 is fitted in the open end of each large-diameter portion 111 in the front face 100a of the pad body 100.

Figure 8:
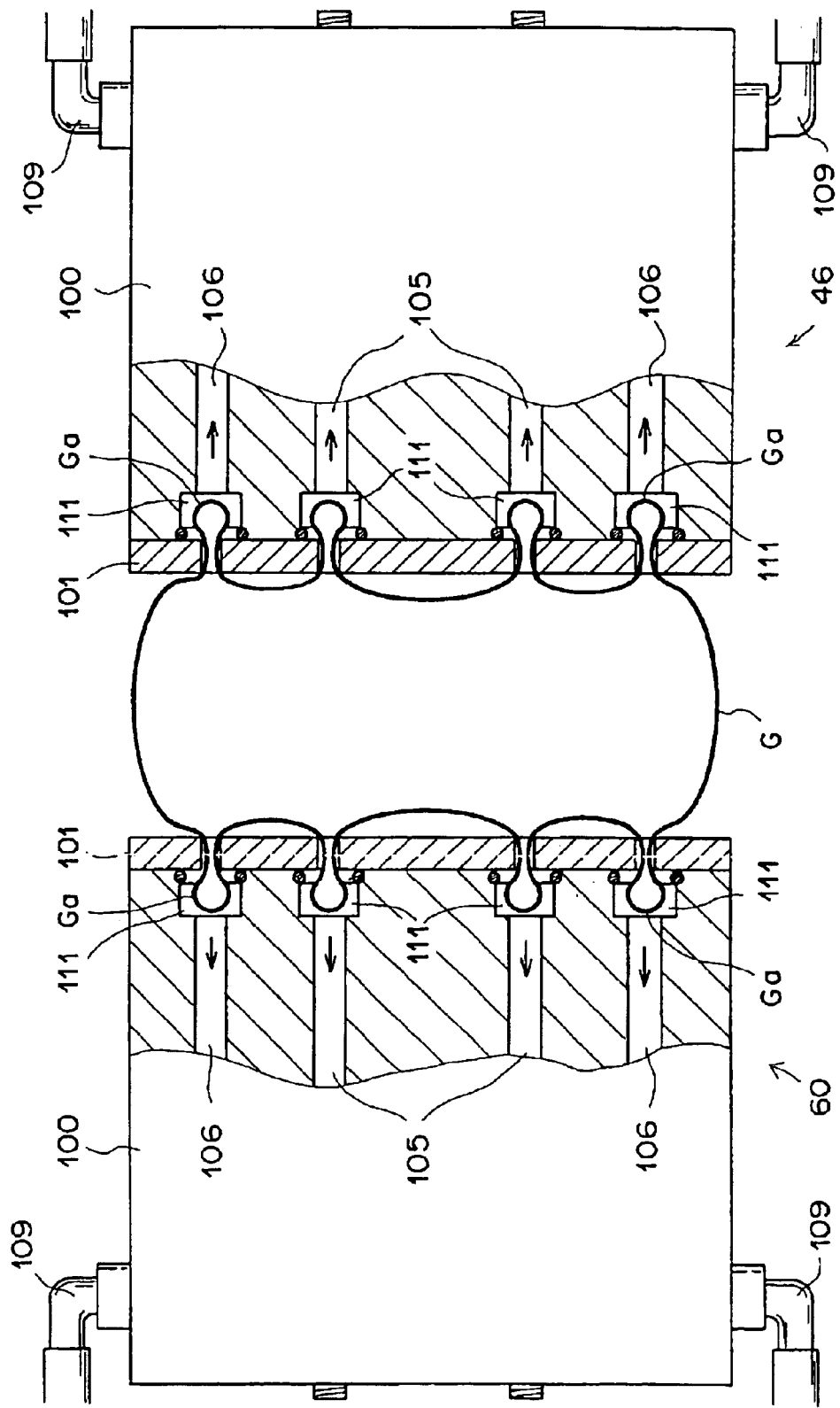
FIG. 8 is a plan view partly in cross-section showing a glove held by the first suction pad shown in FIGS. 7A to 7C with its mouth opened.

When the first and second suction pads 46 and 60 are provided with the large-diameter portions 111 behind the suction holes 102 and 103, the parts of the glove G attracted by suction at the suctions holes 102 and 103 are drawn into the large-diameter portion 111 and inflated therein as shown in FIG. 8. The inflated portions Ga function as a stopper and prevent the glove G from falling off the suction faces 46a and 60a of the suction pads 46 and 60 without increasing the vacuum applied to the respective suction holes 102 and 103.

By increasing the inner diameter of each of the suction holes away from the suction faces 46a and 60a inward, the suction forces acting on the suction holes 102 and 103 for a given vacuum applied to the air passages 105 and 106 can be enhanced.

Figure 9A:
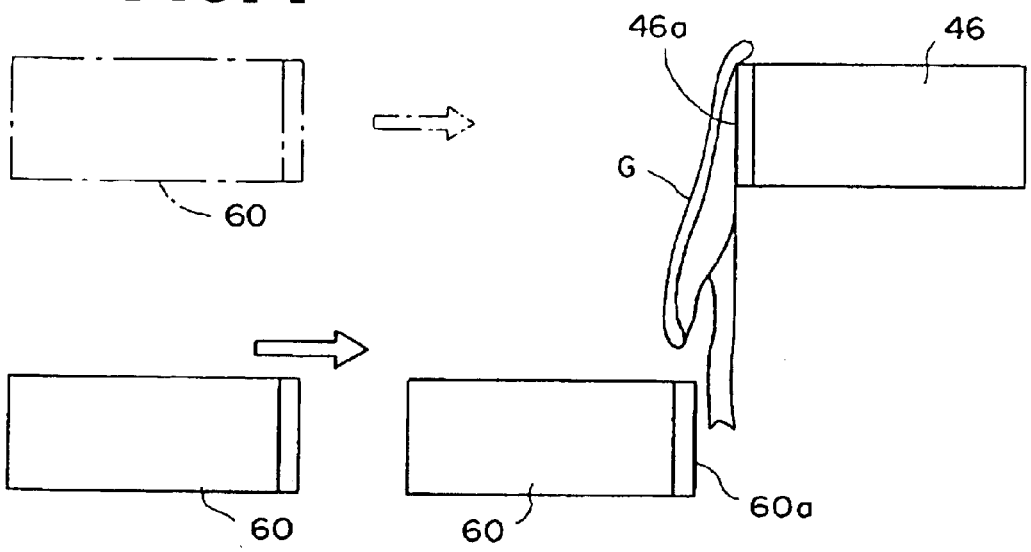
FIGS. 9A to 9C are views for illustrating a preferred modification of the path along which the second suction pad is to be moved to open the mouth of the glove.
Figure 9B:
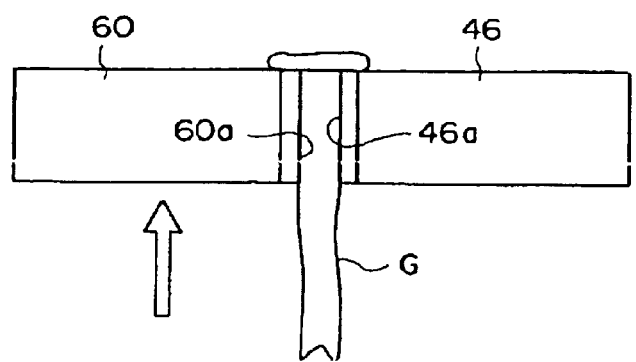
Figure 9C:
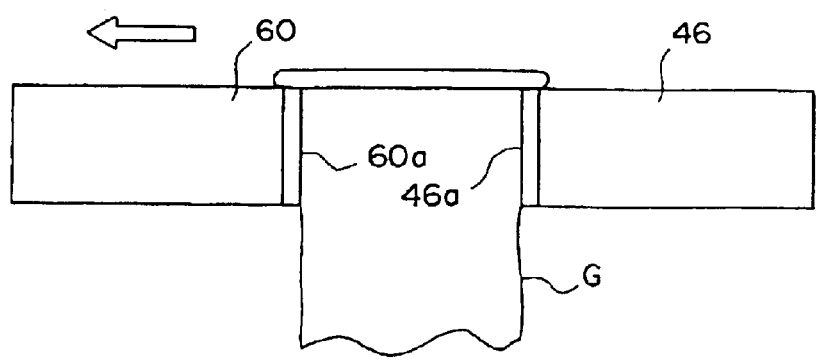

FIGS. 9A to 9C shows a preferred path of the second suction pad 60 through which the second suction pad 60 is moved to open the mouth of the glove G.

That is, in the state where the first suction pad 46 is moved to the stand-by position holding the right ply of the glove G by suction near the mouth of the glove G, the portion of the left ply near the mouth of the glove G can be hung with the inner side of the mouth directed toward the second suction pad 60 as shown in FIG. 9A. This can occur especially when the glove G is flexible, e.g., the glove G is of rubber. When the second suction pad 60 is at the level equal to the first suction pad 46 in its stand-by position as shown by the chained line in FIG. 9A and is horizontally moved toward the first suction pad 46, the first and second suction pads 46 and 60 cannot be properly brought into contact with the opposite plies of the glove G but can be brought into contact with the opposite sides of the right ply of the glove G.

In order to avoid this problem, the stand-by position of the second suction pad 60 is set below the stand-by position of the first suction pad 46 as shown by the solid line in FIG. 9A and the second suction pad 60 is once moved horizontally toward the glove G and thereafter moved upward to the level of the first suction pad 46 so that the second suction pad 60 forces upward the hanging portion of the left ply near the mouth of the glove G along the corresponding portion of the right ply when it is moved upward. In this manner, the first and second suction pads 46 and 60 can be surely brought into contact with the opposite plies of the glove G near to the mouth of the glove G as shown in FIG. 9B, whereby the mouth of the glove G can be surely opened in response to subsequent movement of the second suction pad 60 away from the first suction pad 46 as shown in FIG. 9C.

The chuck 14 for holding the glove G with its mouth kept opened left and right and the chuck drive mechanism 32 will be described with reference to FIGS. 10 to 16, hereinbelow.

Figure 12:
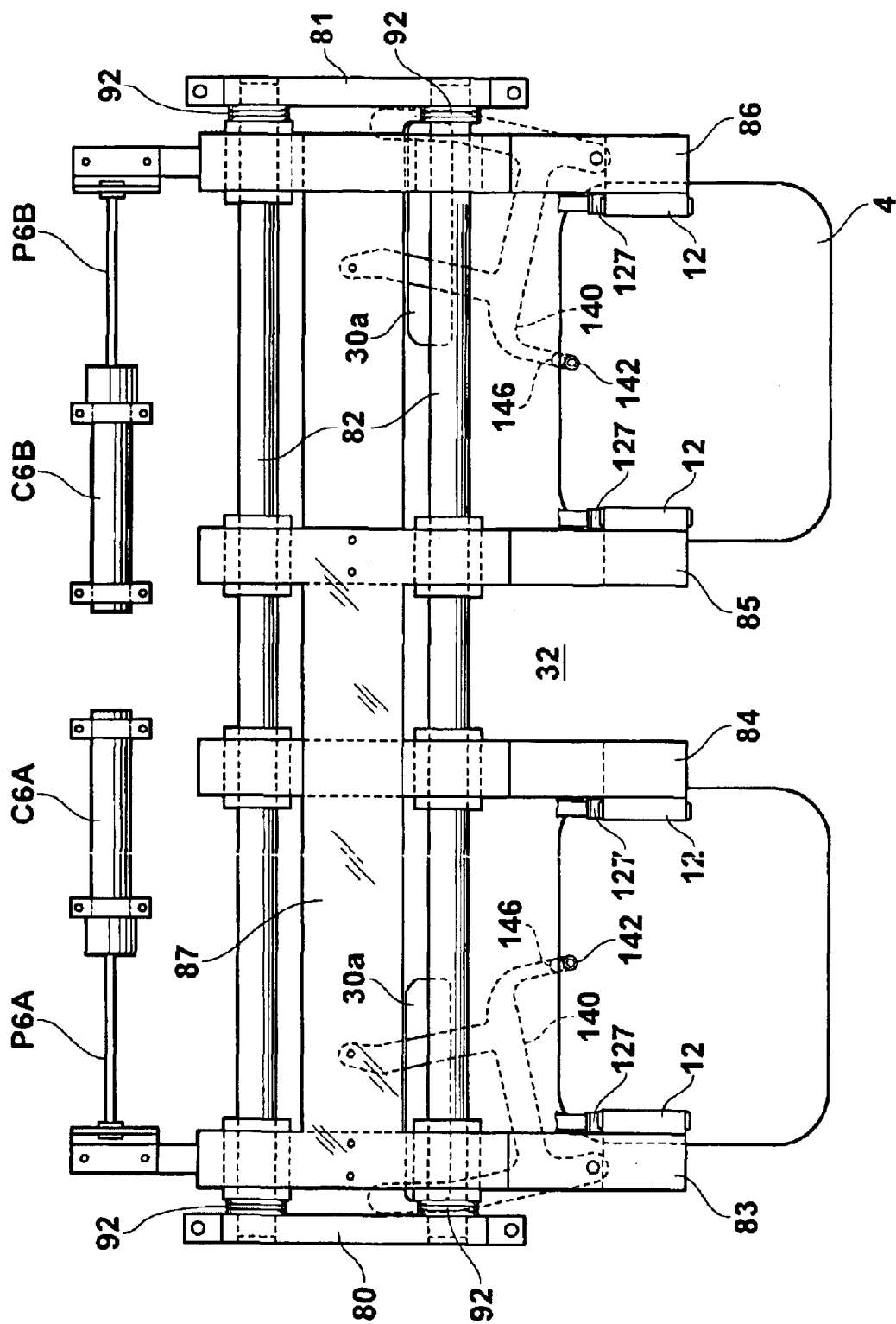
FIG. 12 is a plan view showing the chuck drive mechanism in a state where the movable claws of the chuck are in the glove holding position.

FIGS. 10 and 11 are a plan view and a front view showing a state where the movable claws 12 of each chuck 14 is in the stand-by position substantially at the center of the hand insertion opening 4, and FIGS. 12 and 13 are a plan view and a front view showing a state where the movable claws 12 of each chuck 14 are in their holding position where they are associated with the stationary claws 10 to hold the glove G with the mouth kept opened left and right.

The chuck drive mechanism 32 comprises left and right support plates 80 and 81 spaced from each other left and right, a pair of guide rods 82 extending left and right between the support plates 80 and 81 spaced from each other back and forth, and four movable claw carriers 83 to 86 to each of which one of the movable claws 12 are fixed and which are slidable along the guide rods 82. The movable claw carriers 83 and 85 to which the left movable claws of the respective chucks 14 are fixed are connected with each other by a connecting plate 87 to be moved integrally with each other, and the movable claw carriers 84 and 86 to which the right movable claws of the respective chucks 14 are fixed are connected with each other by a connecting plate 88 to be moved integrally with each other.

The piston rods P6A and P6B of cylinders C6A and C6B are respectively connected to the leftmost movable claw carrier 83 and the rightmost movable claw carrier 86.

When both the piston rods P6A and p6B are retracted, the movable claws 12 of each chuck 14 are in the stand-by position substantially at the center of the hand insertion opening 4 where the claws are disposed near to each other as shown in FIGS. 10 and 11 so that the movable claws 12 can be easily inserted into the glove G through the mouth thereof when the glove G is brought to the hand insertion position with its mouth opened by the first and second suction pads 46 and 60. When the piston rods P6A and P6B are projected with the movable claws 12 inserted into the mouth of the glove G, the movable claws 12 are moved toward the respective stationary claws 10 to the holding position, where the glove G is held between the left movable claw and the left stationary claw and between the right movable claw and the right stationary claw with its mouth kept opened as shown in FIGS. 12 and 13.

Figure 14A:
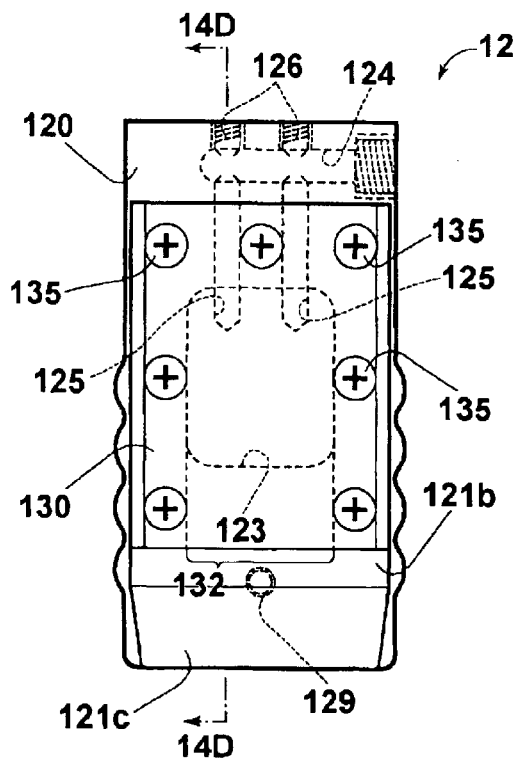

FIGS. 14A to 14D are a front view, a side view, and a plan view of the movable claw 12 and a cross-sectional view taken along line 14D—14D in FIG. 14A. Two of the four movable claws 12 are as shown in FIGS. 14A to 14D and the other two movable claws 12 are of the mirror image of the movable claw shown in FIGS. 14A to 14D.

The movable claw 12 is provided with an air-blow port 132 on its rear side (the side opposite to the side holding the glove G). The air-blow port 132 is like a slit in shape and for blowing air into the glove G when putting the glove G on the hand. The movable claw 12 comprises a body portion 120 which is Γ-shaped in a side view and a lid member 130 which is mounted on the body portion 120 to form the air-blow port 132 at its lower end.

Figure 14B:
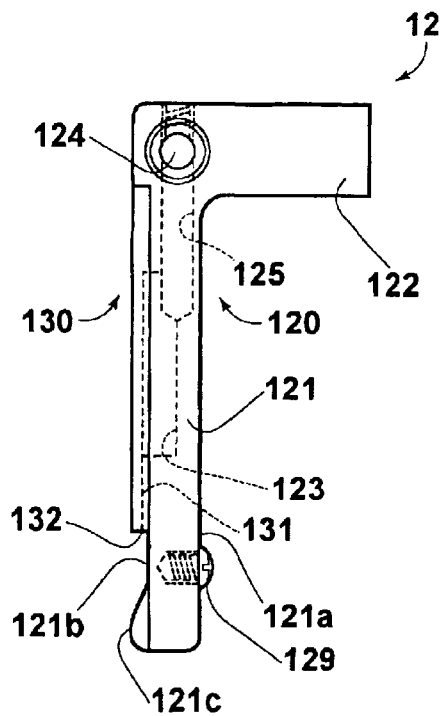
Figure 14C:
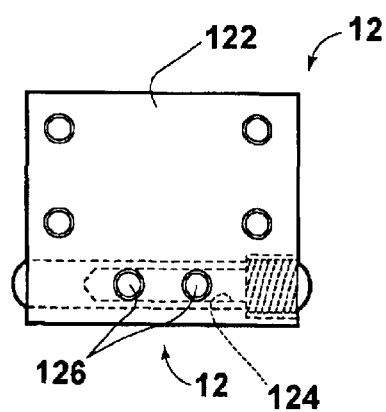
Figure 14D:
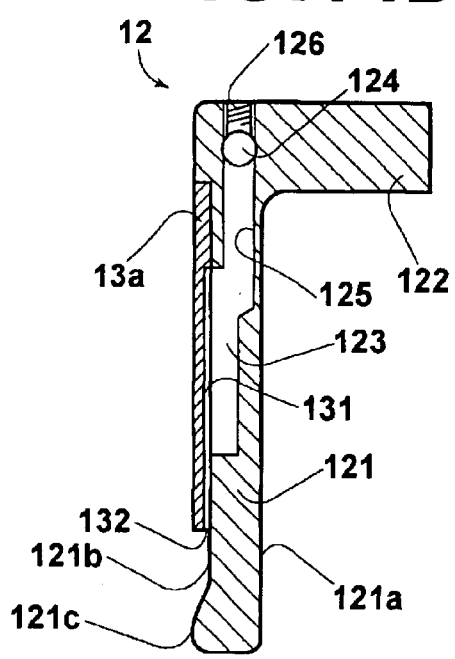

The body portion 120 of the movable claw 12 comprises a flat vertical plate portion 121 which extends up and down and is provided with a flat glove holding surface 121a which faces rightward in FIGS. 14B and 14D and a horizontal plate portion 122 which horizontally extends from the upper end of the vertical plate portion 121 and is fixed to the lower surface of the movable claw carrier. A recessed portion 123 is formed on a flat rear surface 121b of the vertical plate portion 121 opposite to the glove holding surface 121a and the lid member 130 is fixed to the body portion 120 of the movable claw 12 by seven countersunk screws 135 to cover the recessed portion 123.

On the inner surface of the lid member 130, a shallow recessed portion 131 is formed. The shallow recessed portion 131 substantially conforms to the recessed portion 123 of the vertical plate portion 121 at its upper portion and extends to the lower end of the lid member 130 beyond the lower end of the recessed portion 123 of the vertical plate portion 121 to form the slit-like air-blow port 132 between the lid member 130 and the rear surface 121b of the vertical plate portion 121. The part of the rear surface 121b of the vertical plate portion 121 below the air-blow port 132 gradually protrudes toward the lower end of the body portion 120 to form a slant surface 121c facing obliquely upward.

A round screw 129 is screwed in a central portion of the lower portion of the glove holding surface 121a of the body portion 120 of the movable claw 12, and a small hole (not shown) is formed in the glove holding surface of the stationary claw 10 to receive the head of the screw 129. By forcing a portion of the glove G near its mouth into the small hole by the head of the round screw 129, the glove G is held. A friction member, such as of rubber, may be bonded to at least one of the opposed surfaces of the stationary claw 10 and the movable claw 12 in order to increase the glove holding force.

The vertical plate portion 121 of the body portion 120 of the movable claw 12 is provided, in its upper portion, with a hole 124 which extends horizontally from one side thereof to a midway and a pair of holes 125 extend from the upper surface of vertical plate portion 121 to the recessed portion 123 through the hole 124. Since the open ends of the holes 125 are closed by plugs 126, air passages which connect the inlet of the hole 124 and the recessed portion 123 are formed inside the movable claw 12. A nipple 127 (FIGS. 10 and 12) is screwed into the inlet of the hole 124 and is communicated with a pressurized air source by way of an electromagnetic valve opened and closed at a cycle of 3 to 6 Hz. With this arrangement, air is intermittently blown through the air-blow port 132 at a cycle of 3 to 6 Hz (preferably not lower than 4 Hz and not higher than 5 Hz) and deflected by the slant surface 121c obliquely downward into the glove G.

Short coiled springs 92 are fitted on the guide rods 82, one on one of the guide rods 82 between the leftmost movable claw carrier 83 and the opposed support plate 80, another on the other of the guide rods 82 between the leftmost movable claw carrier 83 and the opposed support plate 80, another on one of the guide rods 82 between the rightmost movable claw carrier 86 and the opposed support plate 81, and the other on the other of the guide rods 82 between the rightmost movable claw carrier 86 and the opposed support plate 81. When the movable claw carriers 83 and 86 are in the holding position, the coiled springs 92 are compressed and urge the movable claws 12 toward the stand-by position.

That is, when air supply to the cylinders C6A and C6B is cut and the force holding the movable claws 12 in the holding position becomes lower than the force of the coiled springs 92, the movable claw carriers 83 to 86 are slightly displaced toward the stand-by position under the force of the coiled springs 92 and the glove G is released from the chucks 14, whereby the hands can be drawn out from the hand insertion opening 4 together with the gloves G.

Figure 16:
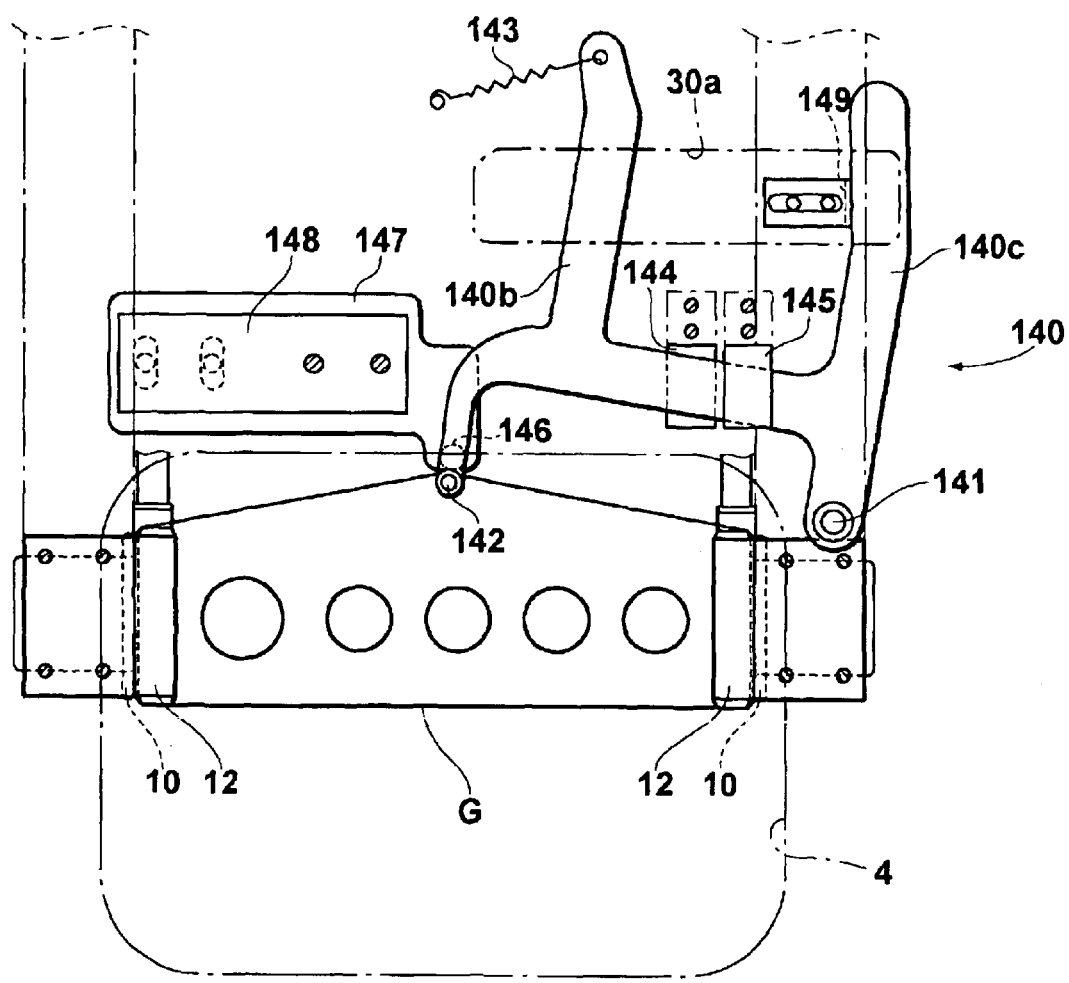
FIG. 16 is an enlarged plan view showing an important part of the right half of FIG. 12 together with the glove.

In this particular embodiment, a center chuck 140 which expands forward (upward as seen in FIG. 16) a central portion of the mouth of the glove G is provided in addition to the chuck 14 which opens left and right the mouth of the glove G.

Figure 15:
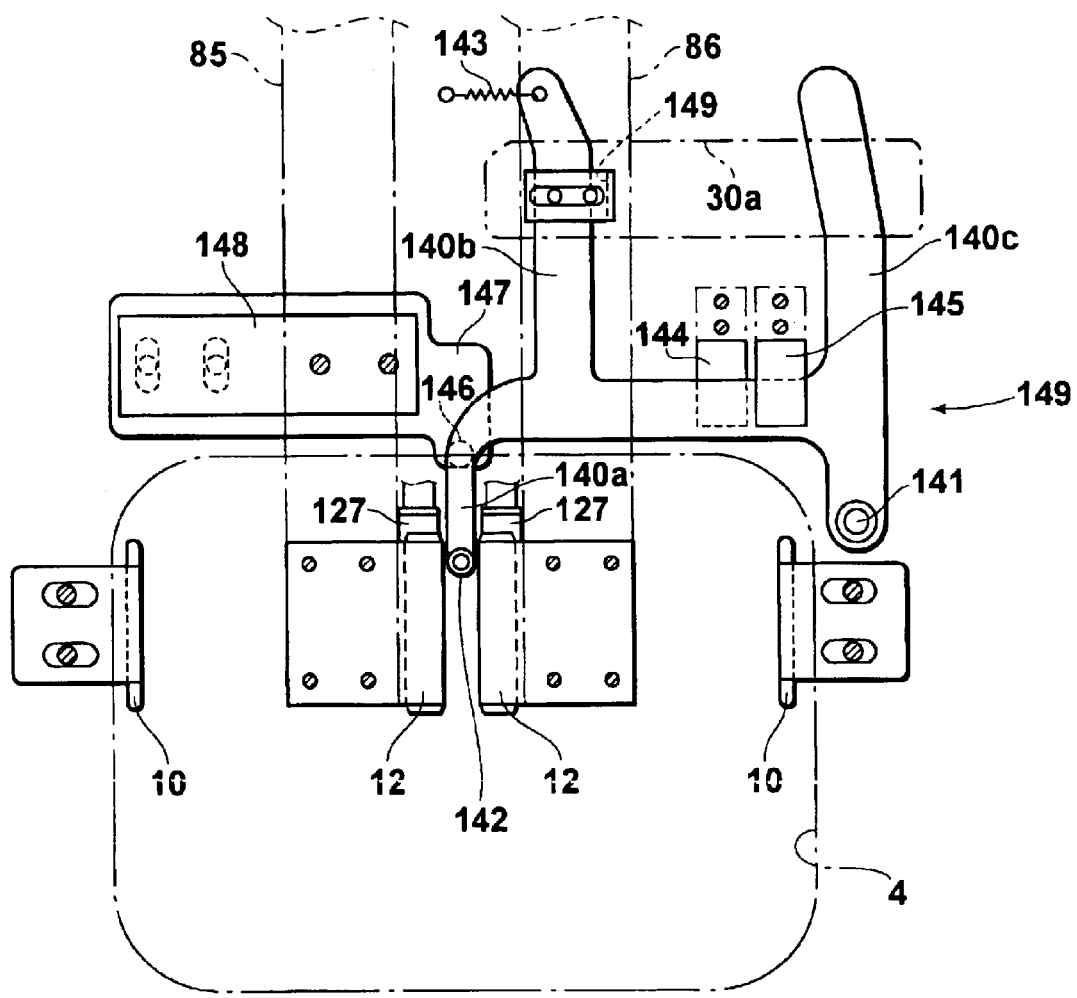
FIG. 15 is an enlarged plan view showing an important part of the right half of FIG. 10.

FIG. 15 is an enlarged plan view showing an important part of the right half of FIG. 10 when the movable claws 12 are in the stand-by position, and FIG. 16 is an enlarged plan view showing an important part of the right half of FIG. 12 when the movable claws 12 are in the glove holding position.

The center chuck 14 supported for rotation on a shaft 141 extending downward from the lower side of the frame 30 as shown in FIG. 15 comprises an arcuate arm portion 140a interposed between the movable claws 12 which are in the stand-by position. A clamp pin 142 which is in such a length that will allow the clamp pin 142 to be inserted into the glove G through the mouth of the glove G held by the chuck 14 is suspended from the tip of the arm portion 140a. Further, the center chuck 140 comprises a pair of arm portions 140b and 140c extending opposite to the arm portion 140a and is counterclockwise (as seen in FIG. 15) urged about the shaft 141 by a spring 143 which is tensed between the frame 30 and the arm portion 140b.

The center chuck 140 is interposed between lower and upper stopper plates 144 and 145 provided on the lower side of the frame 30 to be slidable relatively to the stopper plates 144 and 145 and rotatable in a plane parallel to the lower side of the frame 30 at a predetermined distance therefrom. A plate member 147 is fixed to the lower side of the frame 30 with a spacer 148 intervening therebetween. A clamp pin receiver pin 146 extends downward from one end of the plate member 147 in a position where the clamp pin 142 and the clamp pin receiver pin 146 pinches therebetween the mouth of the glove G when the center chuck 140 is rotated from the stand-by position shown in FIG. 15 to the operative position shown in FIG. 16.

A drive plate 146 is provided on the lower side of each of the outer movable claw carriers 83 and 86 and is brought into abutment against the inner edge of the arm portion 140c of the center chuck 140 in response to movement of the movable claw carrier to rotate the center chuck 140 from the stand-by position shown in FIG. 15 to the operative position shown in FIG. 16, where the clamp pin 142 and the clamp pin receiver pin 146 pinches hold therebetween the mouth of the glove G, overcoming the spring 143.

As can be understood from the description above, in the state shown in FIGS. 12, 13 and 16, the mouths of the left and right gloves G are expanded by chucks 14 let and right and expanded forward (upward as seen in FIG. 16) by the center chucks 140, whereby insertion of the hands into the left and right gloves G is facilitated. Further, since air is intermittently blown toward the center of the glove G through the air-blow opening 132 (FIG. 13) with the hand inserted into the glove G to pulsatively inflate the glove G, a thin glove of latex, raw rubber, or the like adhering to the hand in a dripping wet state can be separated from the hand and the air can reach the tips of the fingers of the glove, whereby a glove can be readily and rapidly put on a hand.

Figure 17:
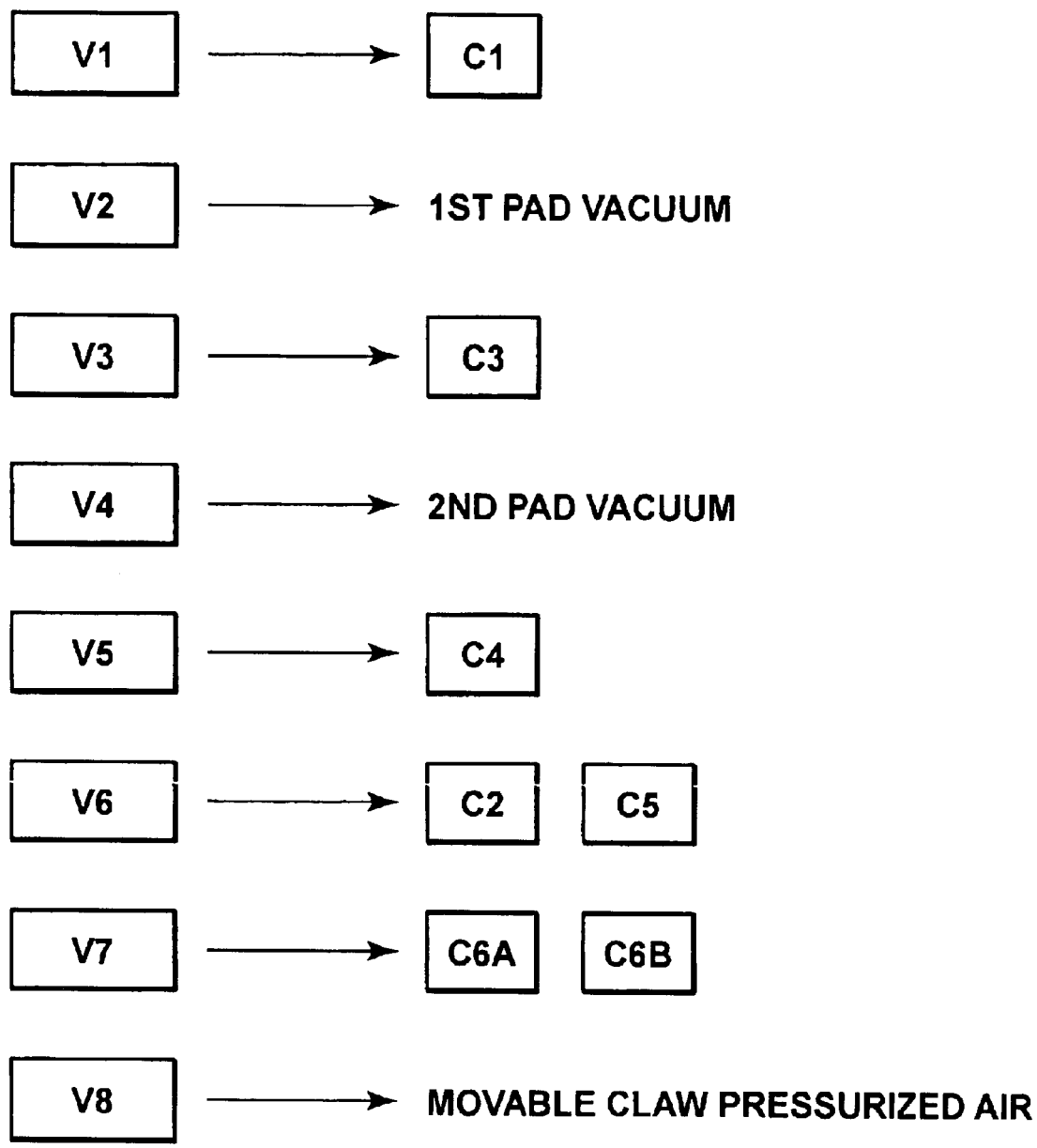
FIG. 17 is a block diagram showing the control system of the automatic gloving apparatus of this embodiment.

FIG. 17 is a block diagram of the automatic gloving apparatus of this embodiment. In this apparatus, air is supplied to the seven air cylinders C1 to C5, C6A and C6B and to the movable claws 12 and vacuum is supplied to the first and second suction pads 46 and 60 by way of eight electromagnetic valves V1 to V8.

Operation of the automatic gloving apparatus 1 of this embodiment will be described with reference to FIG. 17, hereinbelow.

A casing 6 of a glove stack 5 is first set in each of the left and right glove storage portions 8.

(1) Then the power switch 18 is turned on to lit the power lamp 20 and the NG lamp 24.

(2) When the foot switch 28 is subsequently pushed, the valve V1 is operated to retract downward the piston rod P1 of the cylinder C1, whereby the glove conveyor arms 34 are lowered from the stand-by position 34S shown in FIG. 6 to the lowermost position 34D, where the arm bodies 34a are held substantially horizontal, and the first suction pad 46 and the attitude control plate 48 are in contact with the upper surface of the glove stack 5.

(3) Then the valve V2 is turned on, and the uppermost glove G in the glove stack 5 is held by suction at a portion near to the mouth thereof by the first suction pad 46.

(4) The valve V1 is switched and the piston rod P1 of the cylinder C1 is projected upward to return the glove conveyor arms 34 to the stand-by position 34S. The glove conveyor arms 34 are temporarily stopped in the stand-by position. Thus the gloves G are held high with their mouths directed upward as shown in FIG. 3.

(5) Then the valve V3 is operated to retract the piston rod P3 to move the second suction pads 60 toward the respective first suction pads 46, whereby the second suction pads 60 are brought into abutment against the left ply of the glove G at a part near to the mouth.

(6) Thereafter the valve V4 is turned on and vacuum is applied to the second suction pads 60 and the second suction pads 60 holds by suction the left plies of the glove G at a part near to the mouth.

(7) In this state, the valve V5 is operated and the piston rod P4 of the cylinder C4 is projected to retract the second suction pads 60 halfway, whereby the mouths of the respective gloves G are opened back and forth.

(8) Then the valve V6 is operated to projects the piston rods P2 and P5 of the cylinders C2 and C5, whereby the gloves G are moved upward to the hand insertion position with their mouths opened and each pair of movable claws 12 are inserted into the glove G.

(9) The valve C7 is operated to project the piston rods P6A and P6B of the cylinders C6A and C6B to move the movable claw carriers 83 and 86 so that the movable claws 12 are associated with the opposed stationary claws 10 to hold the mouths of the gloves G with the mouths of the gloves G opened left and right. At the same time, the coiled springs 92 are compressed.

(10) The valves V2 and V4 are turned off and vacuum supply to the first and second suction pads 46 and 60 is cut, and at the same time, the valves V3 and V6 are switched so that the piston rod P3 is projected and the piston rods P2 and P5 are retracted, whereby the glove conveyor arms 34 are returned to the stand-by position 34S together with the first suction pads 46 and the second suction pads 60 are returned to the initial position.

(11) When the first and second suction pads 46 and 60 are lowered, the OK lamp 26 (a blue lamp) is lit in place of the NG lamp 24 to indicate that hands may be inserted into the hand insertion openings 4.

(12) When that the hands have been inserted into the gloves G through the hand insertion openings 4 is detected by a sensor, the valve 8 is turned on and off at a cycle of 3 to 6 Hz (preferably not lower than 4 Hz and not higher than 5 Hz) and air is intermittently blown through the air-blow port to pulsatively inflate the glove G. At the same time, a timer is started to count, for instance, 3 seconds, before the timer expires, the left and right hands are gloved. The time for which the air is blown can be adjusted according to the skillfulness of the user.

(13) When the timer ends counting, the valve V8 is turned off and air blow from the movable claws 12 is stopped, and the valve V7 is operated to cut air pressure to the cylinders C6A and C6B, whereby the movable claws 12 are slightly moved away from the stationary claws 10 to release the gloves G and to allow the gloved hands to be drawn out the hand insertion openings 4.

When the user gets familiar to this apparatus, the user can put the gloves G on his or her hands before the timer ends counting, e.g., within 2 seconds whereas the timer is set at 3 seconds. In such a case, the foot switch 28 is pushed again, whereby the valve V8 is turned off and the valve V7 is operated to cut air pressure to the cylinders C6A and C6B

(14) That the gloved hands are drawn out the hand insertion openings is detected by a sensor and the NG lamp 24 is lit in place of the OK lamp 26, and at the same time, the piston rods P6A and P6B are retracted to return the movable claws 12 to the stand-by position shown in FIGS. 10 and 11.

When the stand-by position of the second suction pad 60 is set below the stand-by position of the first suction pad 46 as shown by the solid line in FIG. 9A and the second suction pad 60 is once moved horizontally toward the glove G and thereafter moved upward to the level of the first suction pad 46 so that the second suction pad 60 forces upward the hanging portion of the left ply near the mouth of the glove G along the corresponding portion of the right ply, for instance, the cylinder C5 is not fixed to the housing 2 but to a movable table which is movable up and down and driven by an additional air cylinder.

Though, in the embodiment described above, air is blown into the glove G through the air-blow port 132 formed in the movable claw 12, air may be blown through an air nozzle fixed to the movable claw carrier or through an air nozzle disposed above the mouth of the glove G. However, it is most preferred that air be blown into the glove G through the air-blow port 132 formed in the movable claw 12 as shown in FIGS. 13 and 14.

As can be understood from the description above, since the automatic gloving apparatus of this embodiment comprises a first suction pad 46 which holds under suction the uppermost one of gloves G stacked in a glove storage portion 8 at the portion near its mouth and conveys the glove G to the hand insertion position, a second suction pad 60 which opens back and forth the mouth of the glove before the first suction pad 46 conveys the glove G to the hand insertion position and is associated with the first suction pad 46 to hold and convey the glove G to the hand insertion position with its mouth kept open, a chuck 14 which opens left and right the mouth of the glove G conveyed to the hand insertion position and holds the mouth of the glove G open so that the hand can inserted into the glove G and a clamp pin 142 which opens forward the mouth of the glove G, gloves can be automatically and continuously put on the hands by simply inserting the hands into the hand insertion openings 4.

Further the hands can be gloved without touching the surface of the gloves, which is much preferred in view of sanitation and disinfection in the case where the gloves are disposable operating gloves used, for instance, in a hospital and food sanitation in the case where the gloves are disposable working gloves used, for instance, in a food processing plant.

Further since the air-blow port 132 is provided in each of the four movable claw 12 which hold the gloves G with the gloves G opened so that the hands can inserted into the gloves, and air is intermittently blown into the glove from inside the glove below the upper edge of the mouth of the glove, air can pulsatively inflate the glove and reach the tips of the fingers of the glove, whereby even a thin glove of raw rubber can be readily and rapidly put on a hand even if the hand is in a dripping wet state.

What is claimed is:

1. An automatic gloving apparatus comprising:
   a glove conveying means configured to remove a glove stored in a glove storage portion in which a plurality of gloves are stored and convey the glove to a hand insertion position where a hand can be inserted into the glove; and
   a glove holding means configured to open a mouth of the glove in the hand insertion position so that a hand can be inserted into the glove through the mouth and hold the glove with the mouth of the glove kept open; and
   an air blow means configured to intermittently blow air into the glove held by the glove holding means,
   wherein, said air blow means is configured to intermittently blow air into the glove on a cycle repeated with a frequency not lower than 3 Hz and not higher than 6 Hz.

2. The automatic gloving apparatus as defined in claim 1, wherein said air blow means is configured to intermittently blow air into the glove on a cycle not lower than 4 Hz and not higher than 5 Hz.

3. The automatic gloving apparatus as defined in claim 1, wherein said air blow means comprises an electromagnetic valve configured to intermittently open an air passage connecting a pressurized air source and an air blow port during each cycle.

4. The automatic gloving apparatus as defined in claim 1, wherein said glove holding means comprises a movable claw which is movable between a stand-by position where it can be inserted into a glove conveyed to the hand insertion position and a glove holding position where it can hold the glove with the mouth of the glove kept open, and
   wherein an air blow port is provided on the movable claw.

5. The automatic gloving apparatus as defined in claim 4, wherein said glove holding means is provided with a fixed claw which is associated with the movable claw to pinch therebetween the mouth of the glove when the movable claw is moved to the glove holding position.

6. The automatic gloving apparatus as defined in claim 4, wherein said glove holding means is further provided with an expansion means configured to expand the mouth of the glove in response to movement of the movable claw from the stand-by position to the glove holding position, in a direction perpendicular to the direction in which the glove holding means is configured to open the mouth.

7. An automatic gloving apparatus comprising:
   a glove conveying means configured to remove a glove stored in a glove storage portion in which a plurality of gloves are stored and convey the glove to a hand insertion position where a hand can be inserted into the glove;
   a glove holding means configured to open a mouth of the glove in the hand insertion position so that a hand can be inserted into the glove through the mouth and hold the glove with the mouth of the glove kept open; and
   an air blow means configured to blow air into the glove held by the glove holding means,
   wherein said glove holding means comprises:
      a movable claw, which is movable between a stand-by position where it can be inserted into a glove conveyed to the hand insertion position and a glove holding position where it can hold the glove with the mouth of the glove kept open; and
      a fixed claw which is associated with the movable claw to pinch therebetween the mouth of the glove when the movable claw is moved to the glove holding position;
   wherein said air blow means includes an air blow port provided on the movable claw.

8. An automatic gloving apparatus comprising:
   a glove conveying means configured to remove a glove stored in a glove storage portion in which a plurality of gloves are stored and convey the glove to a hand insertion position where a hand can be inserted into the glove;
   a glove holding means configured to open a mouth of the glove in the hand insertion position so that a hand can be inserted into the glove through the mouth and hold the glove with the mouth of the glove kept open; and
   an air blow means configured to blow air into the glove held by the glove holding means,
   wherein said glove holding means comprises:
      a movable claw, which is movable between a stand-by position where it can be inserted into a glove conveyed to the hand insertion position and a glove holding position where it can hold the glove with the mouth of the glove kept open; and
      an expansion means configured to expand the mouth of the glove in response to movement of the movable claw from the stand-by position to the glove holding position, in a direction perpendicular to the direction in which the glove holding means opens the mouth, the air blow means including an air blow port provided on the movable claw.

9. An automatic gloving apparatus comprising:
   a glove storage portion where a plurality of gloves are stored;
   a glove conveyor configured to remove a glove and convey the glove to a hand insertion position where a hand can be inserted into the glove; and
   a glove holder configured to open a mouth of the glove in the hand insertion position so that a hand can be inserted into the glove through the mouth and hold the glove with the mouth of the glove kept open;
   said glove holder including a guide rod, a pair of stationary claws spaced out from each other, and a pair of movable claws mounted on said guide rod and capable of moving from side to side relative to said guide rod between said stationary claws, for holding said mouth of the glove between said movable claws and said stationary claws;
   wherein at least one movable claw of said pair of movable claws includes an air blow port on a side thereof opposite to a side holding said mouth of the glove, for blowing air into said glove.

* * * * *